(12) United States Patent
Vaddiraju et al.

(10) Patent No.: US 11,540,750 B2
(45) Date of Patent: Jan. 3, 2023

(54) SYSTEMS AND METHODS FOR PHYSIOLOGICAL CHARACTERISTIC MONITORING

(71) Applicant: MEDTRONIC MINIMED, INC., Northridge, CA (US)

(72) Inventors: Santhisagar Vaddiraju, Plymouth, MN (US); Bejan M. Darbandi, Chanhassen, MN (US); Nicholas S. Mairs, Minneapolis, MN (US); Brian Ross, Maple Grove, MN (US)

(73) Assignee: MEDTRONIC MINIMED, INC, Northridge, CA (US)

( * ) Notice: Subject to any disclaimer, the term of this patent is extended or adjusted under 35 U.S.C. 154(b) by 315 days.

(21) Appl. No.: 16/225,768

(22) Filed: Dec. 19, 2018

(65) Prior Publication Data
US 2020/0196920 A1  Jun. 25, 2020

(51) Int. Cl.
*A61B 5/145* (2006.01)
*A61B 5/0205* (2006.01)
*A61B 5/00* (2006.01)
*A61B 5/01* (2006.01)

(52) U.S. Cl.
CPC ........ *A61B 5/14532* (2013.01); *A61B 5/0022* (2013.01); *A61B 5/01* (2013.01); *A61B 5/0205* (2013.01); *A61B 5/14546* (2013.01); *A61B 5/681* (2013.01); *A61B 5/7275* (2013.01); *A61B 2562/0219* (2013.01)

(58) Field of Classification Search
CPC ........ A61B 5/14532; A61B 2560/0456; A61B 5/6801; A61B 5/1118; A61B 5/7282; A61B 5/746; A61B 5/6833; A61B 5/742; A61B 5/681
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |

(Continued)

FOREIGN PATENT DOCUMENTS

WO   WO-2017091726 A1 * 6/2017 ............. G06F 1/163

*Primary Examiner* — Sean P Dougherty
*Assistant Examiner* — Jonathan E. Cooper
(74) *Attorney, Agent, or Firm* — Weaver Austin Villeneuve & Sampson LLP

(57) ABSTRACT

A physiological characteristic monitoring system includes a physiological characteristic sensor that observes a physiological characteristic and generates sensor signals based on the observation. The physiological characteristic sensor includes a sensor connector. The physiological characteristic monitoring system includes a wearable device to be worn by a user in a first configuration and having a connector to couple to the sensor connector in a second configuration. The wearable device includes a controller that receives the sensor signals from the physiological characteristic sensor in the second configuration and determines a current value of the physiological characteristic based on the sensor signals.

10 Claims, 9 Drawing Sheets

(56) References Cited

U.S. PATENT DOCUMENTS

| | | |
|---|---|---|
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 3,024,201 A1 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 * | 1/2013 | Say .................. A61B 5/1495 |
| | | 600/365 |
| 2007/0123819 A1 | 5/2007 | Mernoe et al. |
| 2010/0160861 A1 | 6/2010 | Causey, III et al. |
| 2016/0029977 A1* | 2/2016 | Di Resta .............. A61B 5/743 |
| | | 600/365 |
| 2016/0100758 A1* | 4/2016 | Jeong .................. G06F 1/163 |
| | | 340/870.07 |
| 2016/0317070 A1* | 11/2016 | Sivaraman .......... A61B 5/1455 |
| 2017/0367627 A1* | 12/2017 | Brister ................ A61B 5/6833 |
| 2018/0056129 A1* | 3/2018 | Narasimha Rao ... A61B 5/7278 |
| 2018/0070824 A1* | 3/2018 | Cronin .............. A61B 5/02055 |
| 2018/0295895 A1* | 10/2018 | Donohoe .............. A61B 5/681 |
| 2019/0110749 A1* | 4/2019 | Forrester ............. A61B 5/6833 |
| 2019/0274603 A1* | 9/2019 | Ringemann ........... G16H 50/20 |

\* cited by examiner

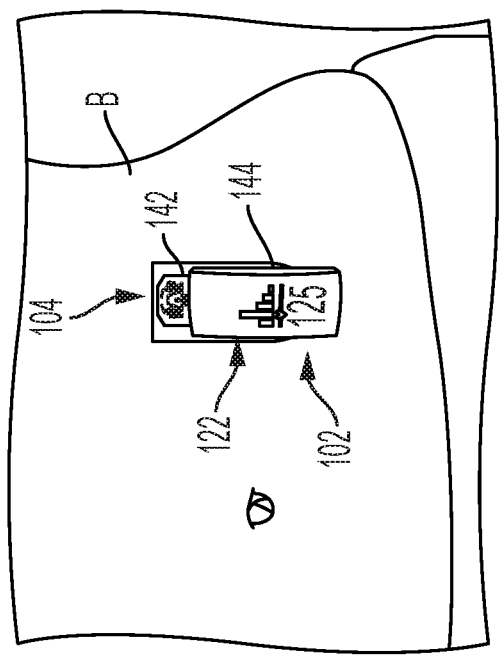
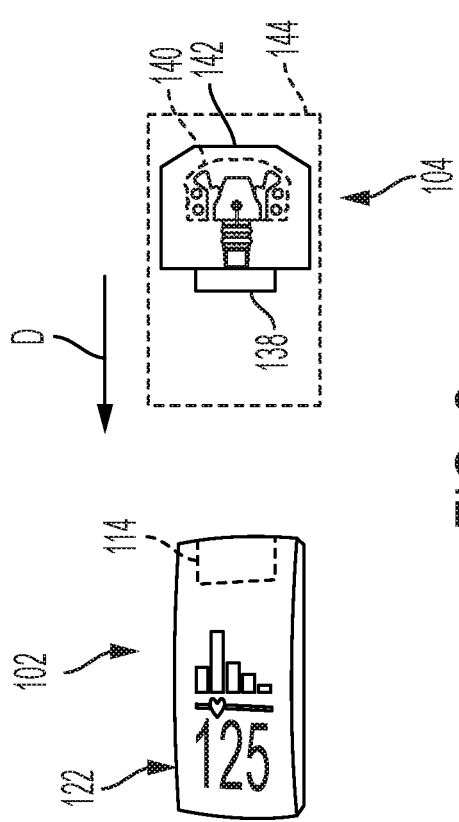

SYSTEMS AND METHODS FOR PHYSIOLOGICAL CHARACTERISTIC MONITORING

FIELD

Embodiments of the subject matter described herein relate generally to systems and methods for monitoring a physiological characteristic. More particularly, embodiments of the subject matter relate to systems and methods for physiological characteristic monitoring, which include a wearable device and a physiological characteristic sensor, such as a blood glucose sensor.

BACKGROUND

Sensors may be employed in the treatment of or monitoring of various medical conditions. In one example, thin film electrochemical sensors are used to test analyte levels in patients or users. More specifically, thin film sensors have been designed for use in obtaining an indication of blood glucose (BG) levels and monitoring BG levels in a diabetic user, with the distal segment portion of the sensor positioned subcutaneously in direct contact with extracellular fluid. Such readings can be especially useful in adjusting a treatment regimen which typically includes regular administration of insulin to the user.

In certain instances, sensors for monitoring BG levels are directed to be used by a medical provider to monitor BG levels continuously over a period of time. In these instances, the medical provider may instruct the user to employ the sensor intermittently over the course of a year. Typically, the BG levels observed by the sensor are provided to the medical provider once the user has completed their use for review and for the adjusting of the treatment regimen.

It may be desirable, however, for the user to observe their BG levels during the use of the sensor. Further, for users who are prescribed intermittent use of the sensor it may be desirable to also track the user's activity levels, sleep cycles, heart rates and other metrics as they use the sensor to provide a correlation between these metrics and the user's BG levels. In addition, for users who are prescribed intermittent use of the sensor, it may be desirable to provide a reusable wearable device that interfaces with the sensor such that the user may not need to purchase hardware with each prescribed use of the sensor.

Accordingly, it is desirable to provide systems and methods for monitoring a physiological characteristic with a reusable wearable device that interfaces with a physiological characteristic sensor, such as a blood glucose sensor, which enables the user to observe their BG levels during use of the sensor and enables the correlation of various metrics of the user with the observed BG levels. Furthermore, other desirable features and characteristics will become apparent from the subsequent detailed description and the appended claims, taken in conjunction with the accompanying drawings and the foregoing technical field and background.

SUMMARY

The techniques of this disclosure generally relate to a physiological characteristic monitoring system that includes a wearable device that interfaces with a physiological characteristic sensor, such as a blood glucose sensor and associated methods.

According to various embodiments, provided is a physiological characteristic monitoring system. The physiological characteristic monitoring system includes a physiological characteristic sensor that observes a physiological characteristic and generates sensor signals based on the observation. The physiological characteristic sensor includes a sensor connector. The physiological characteristic monitoring system includes a wearable device to be worn by a user in a first configuration and having a connector to couple to the sensor connector in a second configuration. The wearable device includes a controller that receives the sensor signals from the physiological characteristic sensor in the second configuration and determines a current value of the physiological characteristic based on the sensor signals.

Also provided according to various embodiments is a physiological characteristic monitoring system. The physiological characteristic monitoring system includes a physiological characteristic sensor that observes a physiological characteristic and generates sensor signals based on the observation. The physiological characteristic sensor includes a sensor connector. The physiological characteristic monitoring system includes a wearable device to be worn by a user in a first configuration and having a connector to couple to the sensor connector in a second configuration. The wearable device includes at least one activity sensor that observes an activity level of the user and generates activity sensor signals based on the observation of the activity level, The wearable device includes a controller that receives the sensor signals from the physiological characteristic sensor in the second configuration, determines a current value of the physiological characteristic based on the sensor signals of the physiological characteristic sensor, and determines a current activity level of the user based on the activity sensor signals of the at least one activity sensor.

Further provided according to various embodiments is a physiological characteristic monitoring system. The physiological characteristic monitoring system includes a physiological characteristic sensor that observes a physiological characteristic and generates sensor signals based on the observation. The physiological characteristic sensor includes a sensor connector. The physiological characteristic monitoring system includes a wearable device to be worn by a user in a first configuration and having a connector to couple to the sensor connector in a second configuration. The wearable device includes a user interface including a display and at least one activity sensor that observes an activity level of the user and generates activity sensor signals based on the observation of the activity level. The wearable device includes a controller that receives the sensor signals from the physiological characteristic sensor in the second configuration and determines a current value of the physiological characteristic based on the sensor signals of the physiological characteristic sensor, that determines a current activity level of the user based on the activity sensor signals of the at least one activity sensor and based on the sensor signals from the physiological characteristic sensor, the controller of the wearable device generates physiological value user interface data for rendering on the display an indication of the current value of the physiological characteristic.

This summary is provided to introduce a selection of concepts in a simplified form that are further described below in the detailed description. The details of one or more aspects of the disclosure are set forth in the accompanying drawings and the description below. Other features, objects, and advantages of the techniques described in this disclosure will be apparent from the description and drawings, and from the claims. This summary is not intended to identify key features or essential features of the claimed subject matter, nor is it intended to be used as an aid in determining the scope of the claimed subject matter.

BRIEF DESCRIPTION OF DRAWINGS

A more complete understanding of the subject matter may be derived by referring to the detailed description and claims when considered in conjunction with the following figures, wherein like reference numbers refer to similar elements throughout the figures.

FIG. 2 is schematic illustration of the wearable device and the physiological characteristic sensor of FIG. 1, in which the wearable device is uncoupled from the physiological characteristic sensor and an attachment device associated with the wearable device is removed;

FIG. 3 is a schematic illustration of the wearable device and the physiological characteristic sensor of FIG. 1, in which the wearable device is coupled to the physiological characteristic sensor in a second configuration, and the wearable device and the physiological characteristic sensor are coupled to a body of a user;

DETAILED DESCRIPTION

Figure 1:
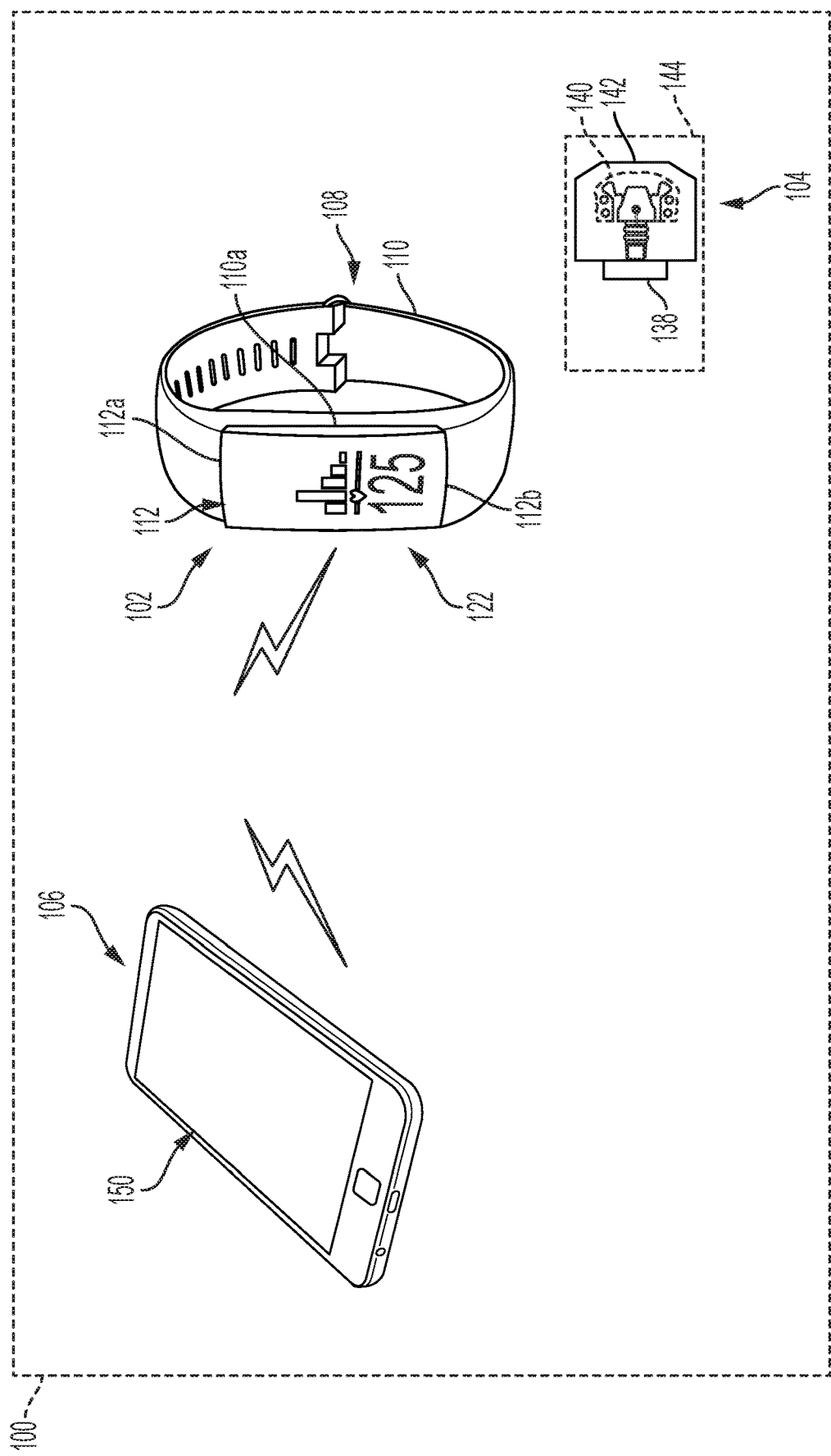
FIG. 1 is a schematic illustration of a physiological characteristic monitoring system, which includes a wearable device that interfaces with a physiological characteristic sensor in accordance with various embodiments and the wearable device is in a first wearable configuration.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Certain terminology may be used in the following description for the purpose of reference only, and thus are not intended to be limiting. For example, terms such as "top", "bottom", "upper", "lower", "above", and "below" could be used to refer to directions in the drawings to which reference is made. Terms such as "front", "back", "rear", "side", "outboard", and "inboard" could be used to describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

As used herein, the term "axial" refers to a direction that is generally parallel to or coincident with an axis of rotation, axis of symmetry, or centerline of a component or components. For example, in a cylinder or disc with a centerline and generally circular ends or opposing faces, the "axial" direction may refer to the direction that generally extends in parallel to the centerline between the opposite ends or faces. In certain instances, the term "axial" may be utilized with respect to components that are not cylindrical (or otherwise radially symmetric). For example, the "axial" direction for a rectangular housing containing a rotating shaft may be viewed as a direction that is generally parallel to or coincident with the rotational axis of the shaft. Furthermore, the term "radially" as used herein may refer to a direction or a relationship of components with respect to a line extending outward from a shared centerline, axis, or similar reference, for example in a plane of a cylinder or disc that is perpendicular to the centerline or axis. In certain instances, components may be viewed as "radially" aligned even though one or both of the components may not be cylindrical (or otherwise radially symmetric). Furthermore, the terms "axial" and "radial" (and any derivatives) may encompass directional relationships that are other than precisely aligned with (e.g., oblique to) the true axial and radial dimensions, provided the relationship is predominately in the respective nominal axial or radial direction. As used herein, the term "transverse" denotes an axis that crosses another axis at an angle such that the axis and the other axis are neither substantially perpendicular nor substantially parallel.

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of schematic, functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of systems, and that the physiological characteristic monitoring systems described herein is merely exemplary embodiments of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following description relates to various embodiments of a physiological characteristic monitoring system that includes a wearable device that interfaces with a physiological characteristic sensor assembly. In one example, the physiological characteristic sensor assembly is a blood glucose sensor. In this example, the system includes the wearable device, which can be coupled to a physiological characteristic sensor, including, but not limited to, a blood glucose sensor, to record observed blood glucose (BG) levels and can be uncoupled from the blood glucose sensor to be worn by the user to monitor the user's activity level, heart rate, sleep pattern, etc. Generally, the wearable device includes one or more coupling portions, which enable the wearable device to be coupled to a wristband, necklace or other mechanism to couple the wearable device to a body of the user when the wearable device is uncoupled from the blood glucose sensor. This enables the user to use and enjoy the wearable device during periods of time in which BG levels are not being sensed. In various embodiments, the wearable device is configured to communicate with a portable electronic device associated with the user, including, but not limited to, a smartphone, tablet, laptop, etc., over a suitable communication protocol to enable the BG levels observed by the blood glucose sensor to be transmitted to a medical provider. It should be noted that while the system is described herein as being used with a blood glucose sensor, it will be understood that the system may be employed with a variety of other removable sensors and/or medical devices. Thus, while the non-limiting examples described below relate to a system for use with a blood glucose sensor used to treat diabetes, embodiments of the disclosed subject matter are not so limited.

With reference to FIG. 1, a schematic diagram of a physiological characteristic monitoring system 100, which includes a wearable device 102 that interfaces with a physiological characteristic sensor 104. As will be discussed, the wearable device 102 is also in communication with an electronic device, which in one example, is a portable electronic device 106. In other examples, the electronic device may be stationary, such as a desktop computer, for example. In the example of FIG. 1, the physiological characteristic sensor 104 is shown physically uncoupled from the wearable device 102 and the wearable device 102 is shown in a first wearable configuration in which the wearable device 102 may be coupled to a body of the user via an attachment device 108. In this example, the attachment device 108 is a wristband 110; however it will be understood that any suitable attachment device 108 may be used to couple the wearable device 102 to the body of the user, including, but not limited to, a necklace, a clasp, a chain, bracelet, hook and loop fastener band, etc. Generally, the attachment device 108 is any device that is capable of physically securing the wearable device 102 to the user, and the attachment device 108 is not a device that is implanted, injected, or otherwise inserted into the body of the user. By coupling the wearable device 102 to the attachment device 108, such as the wristband 110, the wearable device 102 may be enjoyed by the user when the physiological characteristic sensor 104 is disconnected or uncoupled from the wearable device 102. In one example, the wearable device 102 has at least one coupling feature 112, which couples the attachment device 108 to the wearable device 102. In this example, the wearable device 102 has two coupling features 112a, 112b that comprise tabs, which couple the wearable device 102 to a slot 110a defined in the wristband 110 to couple the wristband 110 to the wearable device 102. Generally, the coupling features 112a, 112b are positioned such that the attachment device 108 covers a connector 114 that mechanically and electrically couples the wearable device 102 to the physiological characteristic sensor 104. It should be noted that in other embodiments, the coupling feature 112 may comprise a keyed tab that engages in a corresponding keyed slot defined in the attachment device 108 or wristband 110, or the coupling feature 112 may comprise a permanent magnet, which couples to a corresponding metal portion of the attachment device 108 or wristband 110 to ensure that the wearable device 102 couples to the attachment device 108 in a particular orientation or fixed direction.

With reference to FIG. 2, a schematic diagram illustrates the wearable device 102 with the attachment device 108, in this example the wristband 110 removed, so that the wearable device 102 may be coupled to the physiological characteristic sensor 104. As will be discussed, the wearable device 102 includes the connector 114, which matingly engages with a corresponding sensor connector 138 of the physiological characteristic sensor 104 to physically and electrically couple the physiological characteristic sensor 104 to the wearable device 102. In this example, the wearable device 102 is shown with a female connector, and the physiological characteristic sensor 104 is shown with a male sensor connector; however, it should be understood that the wearable device 102 may include a male connector, and the physiological characteristic sensor 104 may include a female sensor connector. Generally, the connector 114 and the sensor connector 138 enable communication between the wearable device 102 and the physiological characteristic sensor 104, such as the transfer of data, power, commands, etc. between the wearable device 102 and the physiological characteristic sensor 104. In this example, the connector 114 is a Universal Serial Bus (USB) port and the sensor connector 138 is a USB. It should be noted, however, that various other techniques may be used to transfer data and power between the wearable device 102 and the physiological characteristic sensor 104. For example, in certain embodiments, pin-like connectors may be employed to transfer data and power between the wearable device 102 and the physiological characteristic sensor 104. In other embodiments, a magnetic field may be used to transfer data and power between the wearable device 102 and the physiological characteristic sensor 104. In order to couple the wearable device 102 to the physiological characteristic sensor 104, the user moves the physiological characteristic sensor 104 along direction D until the sensor connector 138 is inserted or received within the connector 114 to enable communication and the transfer of data, power, etc. between the physiological characteristic sensor 104 and the wearable device 102.

With reference to FIG. 3, the wearable device 102 and the physiological characteristic sensor 104 are shown coupled together. In FIG. 3, the wearable device 102 is in a second monitoring configuration in which the wearable device 102 cooperates with the physiological characteristic sensor 104 to monitor the BG levels of the user. As shown in FIG. 3, the physiological characteristic sensor 104 is coupled to a body B of the user for monitoring the BG levels of the user, and the wearable device 102 is coupled to the physiological characteristic sensor 104. In one example, as will be discussed, the physiological characteristic sensor 104 and the wearable device 102 are coupled to the body B of the user via an adhesive patch 144. In certain instances, the user may also use an overtape to secure the physiological characteristic sensor 104 and/or the wearable device 102 to the body B of the user in addition to the adhesive patch 144, if desired. The wearable device 102 interfaces with the physiological characteristic sensor 104 for monitoring the BG levels of the user, but is also able to be enjoyed by the user when the physiological characteristic sensor 104 is uncoupled (as shown in FIG. 1).

Figure 4:
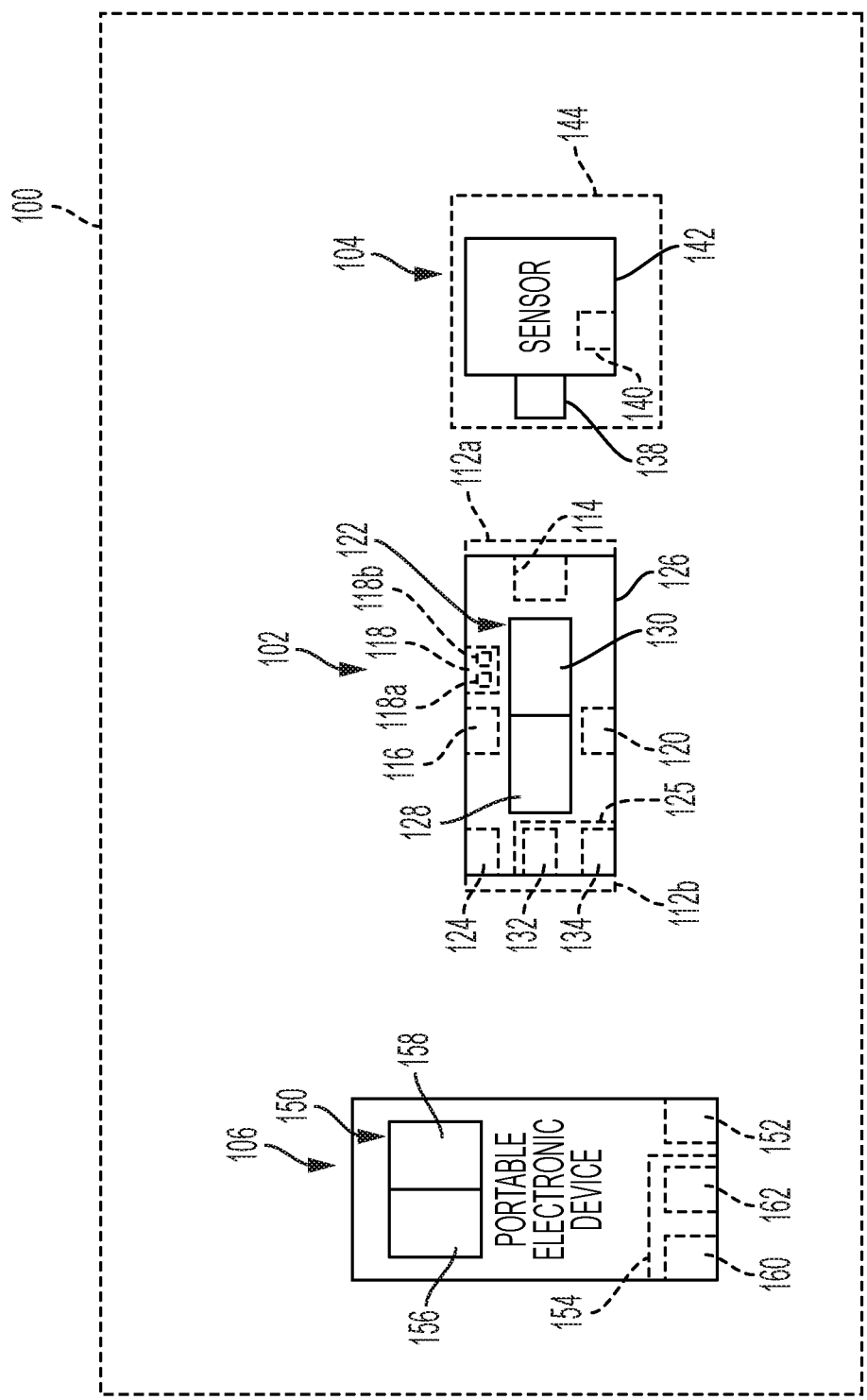
FIG. 4 is a functional block diagram illustrating an exemplary embodiment of the physiological characteristic monitoring system of FIG. 1 according to various teachings of the present disclosure.

With reference to FIG. 4, a functional block diagram of the physiological characteristic monitoring system 100 is shown, which includes the wearable device 102, the physiological characteristic sensor 104 and the portable electronic device 106. In one example, the wearable device 102 includes the connector 114, an activity sensor 116, a heart rate sensor 118, a power source 120, a user interface 122, a communication system 124 and a controller 125. Each of the connector 114, the activity sensor 116, the heart rate sensor 118, the power source 120, the user interface 122, the communication system 124 and the controller 125 are contained in a housing 126, as shown in FIGS. 1-3. The housing 126 may be composed of a biocompatible metal, metal alloy or polymer, and may be formed using casting, molding, stamping, additive manufacturing, etc. The housing 126 may be one-piece or composed of multiple pieces, which are coupled together to retain the connector 114, the activity sensor 116, the heart rate sensor 118, the power source 120, the user interface 122, the communication system 124 and the controller 125 within the housing 126. Each of the connector 114, the activity sensor 116, the heart rate sensor 118, the power source 120, the communication system 124 and the user interface 122 are in communication with the controller 125 over a suitable communication architecture that facilitates the transfer of power, data, commands, etc.

The activity sensor 116 observes a motion level or activity level of the user and generates sensor signals based thereon. In one example, the activity sensor 116 is an accelerometer, which observes a rate of change of velocity or acceleration of the wearable device 102 when the wearable device 102 is coupled to the user. As will be discussed, the controller 125 processes the sensor signals from the activity sensor 116 to determine a current activity level of the user.

The heart rate sensor 118 observes a heart rate of the user and generates sensor signals based thereon. In this example, the heart rate sensor 118 includes a light emitting diode (LED) light source 118a and an LED sensor 118b, and the LED sensor 118b observes an amount of light that reflects back from the skin S of the user when the LED light source 118a is directed toward the skin S of the user. In the example of an LED based heart rate sensor 118, the housing 126 may include a plurality of openings that enable the LED light source 118a to illuminate the skin and the LED sensor 118b to observe the reflections. It should be noted that other techniques may be employed to observe and measure a heart rate of the user. As will be discussed, the controller 125 processes the sensor signals from the LED sensor 118b of the heart rate sensor 118 to determine a current heart rate of the user.

The power source 120 supplies power to the various components of the wearable device 102 and to the physiological characteristic sensor 104 when the physiological characteristic sensor 104 is connected or coupled to the wearable device 102. In one example, the power source 120 supplies power to the controller 125, which in turn supplies power to the user interface 122, the activity sensor 116, the heart rate sensor 118, the communication system 124 and the physiological characteristic sensor 104 (when connected to the wearable device 102) over an architecture that facilitates the transfer of power from the power source 120 to the user interface 122, the activity sensor 116, the heart rate sensor 118, the communication system 124 and the physiological characteristic sensor 104 (when connected to the wearable device 102). The power source 120 generally comprises a rechargeable battery disposed within the housing 126. It should be understood, however, that any power source can be employed to provide power to the user interface 122, the activity sensor 116, the heart rate sensor 118, the communication system 124 and the physiological characteristic sensor 104 (when connected to the wearable device 102) including, but not limited to, disposable batteries, solar cells, etc.

The user interface 122 is in communication with the controller 125 via a suitable communication medium, such as a bus. The user interface 122 may be configured in a variety of ways. In some embodiments, the user interface 122 may include various switches, one or more buttons, a touchscreen interface 128 that may be overlaid on a display 130, a keyboard, an audible device, a microphone associated with a speech recognition system, or various other human-machine interface devices. In one example, the touchscreen interface 128 may receive input from the user, such as an identification of the user, a shutdown request and a number of days of wear for the physiological characteristic sensor 104. The touchscreen interface 128 may include, but is not limited to, a resistive touchscreen panel, a capacitive touchscreen panel, a projected capacitance touchscreen panel, a surface capacitive touchscreen panel, a surface acoustic wave touchscreen panel, etc. Generally, upon the receipt of the touch or input from the user, the touchscreen interface 128 transmits a signal to the controller 125. As will be discussed, the controller 125 processes the signal, and determines whether user identification data, a shutdown request and/or a number of days of wear for the physiological characteristic sensor 104 has been received.

The display 130 comprises any suitable technology for displaying information, including, but not limited to, a liquid crystal display (LCD), organic light emitting diode (OLED), plasma, or a cathode ray tube (CRT). In this example, the display 130 is an electronic display capable of graphically displaying one or more user interfaces under the control of the controller 125. Those skilled in the art may realize other techniques to implement the display 130 in the wearable device 102.

The communication system 124 is configured to wirelessly communicate information to and from the wearable device 102. For example, the communication system 124 is configured to wirelessly communicate data between the wearable device 102 and the portable electronic device 106. The communication system 124 is in communication with the portable electronic device 106 via any suitable communication protocol supported by the portable electronic device 106. In an exemplary embodiment, the communication system 124 is a wireless communication system configured to communicate via a wireless local area network (WLAN) using IEEE 802.11 standards, Bluetooth® or by using cellular data communication. Thus, the communication system 124 includes, but is not limited to, a Bluetooth® transceiver, a radio transceiver, a cellular transceiver, a 2G/3G/4G LTE transceiver and/or a Wi-Fi transceiver. The communication system 124 can also comprise a one-way transmitter. The communication system 124 may also be configured to encode data or generate encoded data. The encoded data generated by the communication system 124 may be encrypted. A security key may be utilized to decrypt and decode the encoded data, as is appreciated by those skilled in the art. The security key may be a "password" or other arrangement of data, finger print, eye fingerprint, face recognition, or DNA recognition that permits the encoded data to be decrypted.

The controller 125 includes at least one processor 132 and a computer readable storage device or media 134. The processor 132 can be any custom made or commercially available processor, a central processing unit (CPU), a graphics processing unit (GPU), an auxiliary processor among several processors associated with the controller 125, a semiconductor based microprocessor (in the form of a microchip or chip set), a macroprocessor, any combination thereof, or generally any device for executing instructions. The computer readable storage device or media 134 may include volatile and nonvolatile storage in read-only memory (ROM), random-access memory (RAM), and keep-alive memory (KAM), for example. KAM is a persistent or non-volatile memory that may be used to store various operating variables while the processor 132 is powered down. The computer-readable storage device or media 134 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 125 in controlling components associated with the physiological characteristic monitoring system 100.

The instructions may include one or more separate programs, each of which comprises an ordered listing of executable instructions for implementing logical functions. The instructions, when executed by the processor 132, receive and process input signals, perform logic, calculations, methods and/or algorithms for controlling the components of the physiological characteristic monitoring system 100, and generate control signals to components of the physiological characteristic monitoring system 100 to output one or more user interfaces, prompts and/or data based on the logic, calculations, methods, and/or algorithms. Although only one controller 125 is shown in FIG. 4, embodiments of the wearable device 102 can include any number of controllers 125 that communicate over any suitable communication medium or a combination of communication mediums and that cooperate to process the sensor signals, perform logic, calculations, methods, and/or algorithms, and generate control signals to control features of the wearable device 102.

In various embodiments, one or more instructions of the controller 125 are associated with the physiological characteristic monitoring system 100 and, when executed by the processor 132, the instructions receive and process signals from the physiological characteristic sensor 104 and determine a value of a physiological characteristic, such as a blood glucose level, of the user. In various embodiments, the instructions of the controller 125, when executed by the processor 132, receive and process signals from the user interface 122 and determine an identity of the user, a shutdown request and a number of days of wear. In various embodiments, the instructions of the controller 125, when executed by the processor 132, receive and process signals from the activity sensor 116 and/or the heart rate sensor 118 and determine an activity level of the user. In various embodiments, the instructions of the controller 125, when executed by the processor 132, determine whether a blood glucose level is greater or less than a threshold and determine whether to output a prompt for medicine. The instructions of the controller 125, when executed by the processor 132, also generate one or more control signals to output one or more user interfaces for the display 130 based on blood glucose levels observed by the physiological characteristic sensor 104.

In one example, the physiological characteristic sensor 104 includes the sensor connector 138, a glucose sensor 140 and a sensor base 142. Many features, aspects, and characteristics of the physiological characteristic sensor 104 and its individual elements are conventional and, as such, will not be described in detail here. It should be noted that the physiological characteristic sensor 104 is not limited to a glucose sensor, but rather, various other physiological characteristic sensors may be employed. The glucose sensor 140 may be provided as an integral part of the sensor base 142. The sensor base 142 gives structural support to the glucose sensor 140, and facilitates entry of the glucose sensor 140 into the body B of the user (FIG. 3). The glucose sensor 140 is an electrochemical sensor that includes the glucose oxidase enzyme, as is well understood by those familiar with glucose sensor technology. The glucose oxidase enzyme enables the glucose sensor 140 to monitor blood glucose levels in a diabetic patient or user by effecting a reaction of glucose and oxygen. Again, although certain embodiments pertain to glucose sensors, the physiological characteristic monitoring system 100 described here can be adapted for use with any one of the wide variety of sensors known in the art. Generally, the glucose sensor 140 is positionable in subcutaneous tissue of the user by an insertion needle of a sensor introducer (not shown) to measure the glucose oxidase enzyme. In this example, the wearable device 102 is coupled to the physiological characteristic sensor 104 such that the sensor introducer may be coupled to the wearable device 102 to insert the glucose sensor 140 into the subcutaneous tissue without interfering with the wearable device 102.

The sensor base 142 is coupled to the sensor introducer prior to the deployment of the glucose sensor 140 into the subcutaneous tissue of the user. The sensor base 142 is also coupled to the adhesive patch 144. The sensor base 142 includes the sensor connector 138 and may also feature electrical and physical interfaces and elements that accommodate the sensor electronics module (not shown), which may include a wireless transmitter that communicates with an infusion pump, the wearable device 102, or the like. In certain embodiments the sensor base 142 is composed at least in part from a plastic material. For the embodiment described here, the bulk of the sensor base 142 is formed as a molded plastic component. In one example, the sensor base 142 is formed from ABS, nylon, an ABS/PC blend, PVC, polytetrafluoroethylene (PTFE), polypropylene, polyether ether ketone (PEEK), polycarbonate, or the like. In this example, the sensor base 142 is composed of polycarbonate. Generally, the sensor connector 138 enables the transfer of data and power between the wearable device 102 and the glucose sensor 140 when the sensor connector 138 is coupled to the connector 114 of the wearable device 102.

The adhesive patch 144 is coupled to the sensor base 142 and affixes the sensor base 142, the glucose sensor 140 and the wearable device 102 to the skin of the user. The adhesive patch 144 may be composed of a flexible and breathable material with one or more adhesive layers, such as cloth, a bandage-like material, and the like. For example, suitable materials could include polyurethane, polyethylene, polyester, polypropylene, polytetrafluoroethylene (PTFE), or other polymers, to which one or more adhesive layers are applied.

In one embodiment, the portable electronic device 106 is a user device, including, but not limited to, a smart phone. It will be understood, however, that the portable electronic device 106 may comprise any user device, including, but not limited to: a mobile computer (e.g., a tablet computer, a laptop computer, or a netbook computer); a video game device; a digital media player; a piece of home entertainment equipment; a digital camera or video camera; a wearable computing device (e.g., smart watch, smart glasses, smart clothing); or the like. Moreover, while the portable electronic device 106 is described herein as being portable or capable of being carried by a user, the user device that interfaces with the wearable device 102 need not be portable. The portable electronic device 106 is realized as a computer-implemented or computer-based device having the hardware, software, firmware, and/or processing logic needed to carry out the various techniques and methodologies described herein. For example, the portable electronic device 106 includes a portable device user interface 150, a portable device communication system 152 and a portable device controller 154. Each of the portable device user interface 150 and the portable device communication system 152 are in communication with the portable device controller 154 over a suitable communication architecture that facilitates the transfer of power, data, commands, etc.

The portable device user interface 150 is in communication with the portable device controller 154. The portable device user interface 150 may be configured in a variety of ways. In some embodiments, the portable device user interface 150 may include various switches, one or more buttons, a touchscreen interface 156 that may be overlaid on a display 158, a keyboard, an audible device, a microphone associated with a speech recognition system, or various other human-machine interface devices. In one example, the touchscreen interface 156 may receive input from the user, such as an identification of the user, a medical provider associated with the user and a request for data. The touchscreen interface 156 may include, but is not limited to, a resistive touchscreen panel, a capacitive touchscreen panel, a projected capacitance touchscreen panel, a surface capacitive touchscreen panel, a surface acoustic wave touchscreen panel, etc. Generally, upon the receipt of the touch or input from the user, the touchscreen interface 156 transmits a signal to the portable device controller 154. As will be discussed, the portable device controller 154 processes the signal, and determines whether a request for data has been received. The portable device controller 154 also processes the signal, determines a user and determines whether a medical provider is associated with the user.

The display 158 comprises any suitable technology for displaying information, including, but not limited to, a liquid crystal display (LCD), organic light emitting diode (OLED), plasma, or a cathode ray tube (CRT). In this example, the display 158 is an electronic display capable of graphically displaying one or more user interfaces under the control of the portable device controller 154. Those skilled in the art may realize other techniques to implement the display 158 in the portable electronic device 106.

The portable device communication system 152 is configured to wirelessly communicate information to and from the portable electronic device 106. For example, the portable device communication system 152 is configured to wirelessly communicate data between the wearable device 102 and the portable electronic device 106. The portable device communication system 152 is in communication with the wearable device 102 via any suitable communication protocol supported by the wearable device 102. In an exemplary embodiment, the portable device communication system 152 is a wireless communication system configured to communicate via a wireless local area network (WLAN) using IEEE 802.11 standards, Bluetooth® or by using cellular data communication. Thus, the portable device communication system 152 includes, but is not limited to, a Bluetooth® transceiver, a radio transceiver, a cellular transceiver, a 2G/3G/4G LTE transceiver and/or a Wi-Fi transceiver. The portable device communication system 152 may also be configured to encode data or generate encoded data. The encoded data generated by the portable device communication system 152 may be encrypted. A security key may be utilized to decrypt and decode the encoded data, as is appreciated by those skilled in the art. The security key may be a "password" or other arrangement of data, finger print, eye fingerprint, face recognition, or DNA recognition that permits the encoded data to be decrypted.

The portable device controller 154 includes at least one processor 160 and a computer readable storage device or media 162. The processor 160 can be any custom made or commercially available processor, a central processing unit (CPU), a graphics processing unit (GPU), an auxiliary processor among several processors associated with the portable device controller 154, a semiconductor based microprocessor (in the form of a microchip or chip set), a macroprocessor, any combination thereof, or generally any device for executing instructions. The computer readable storage device or media 162 may include volatile and nonvolatile storage in read-only memory (ROM), random-access memory (RAM), and keep-alive memory (KAM), for example. KAM is a persistent or non-volatile memory that may be used to store various operating variables while the processor 160 is powered down. The computer-readable storage device or media 162 may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the portable device controller 154 in controlling components associated with the physiological characteristic monitoring system 100.

The instructions may include one or more separate programs, each of which comprises an ordered listing of executable instructions for implementing logical functions. The instructions, when executed by the processor 160, receive and process input signals, perform logic, calculations, methods and/or algorithms for controlling the components of the physiological characteristic monitoring system 100, and generate control signals to components of the physiological characteristic monitoring system 100 to output one or more requests and/or data based on the logic, calculations, methods, and/or algorithms. Although only one portable device controller 154 is shown in FIG. 4, embodiments of the portable electronic device 106 can include any number of portable device controllers 154 that communicate over any suitable communication medium or a combination of communication mediums and that cooperate to process the sensor signals, perform logic, calculations, methods, and/or algorithms, and generate control signals to control features of the portable electronic device 106.

In various embodiments, one or more instructions of the portable device controller 154 are associated with the physiological characteristic monitoring system 100 and, when executed by the processor 160, the instructions receive and process signals from the wearable device 102 and receive data associated with the user. In various embodiments, the instructions of the portable device controller 154, when executed by the processor 160, receive and process signals from the portable device user interface 150 and determine a medical provider associated with the user. In various embodiments, the instructions of the portable device controller 154, when executed by the processor 160, receive data from the wearable device 102 and output data and/or alerts to the medical provider associated with the user.

Figure 5:
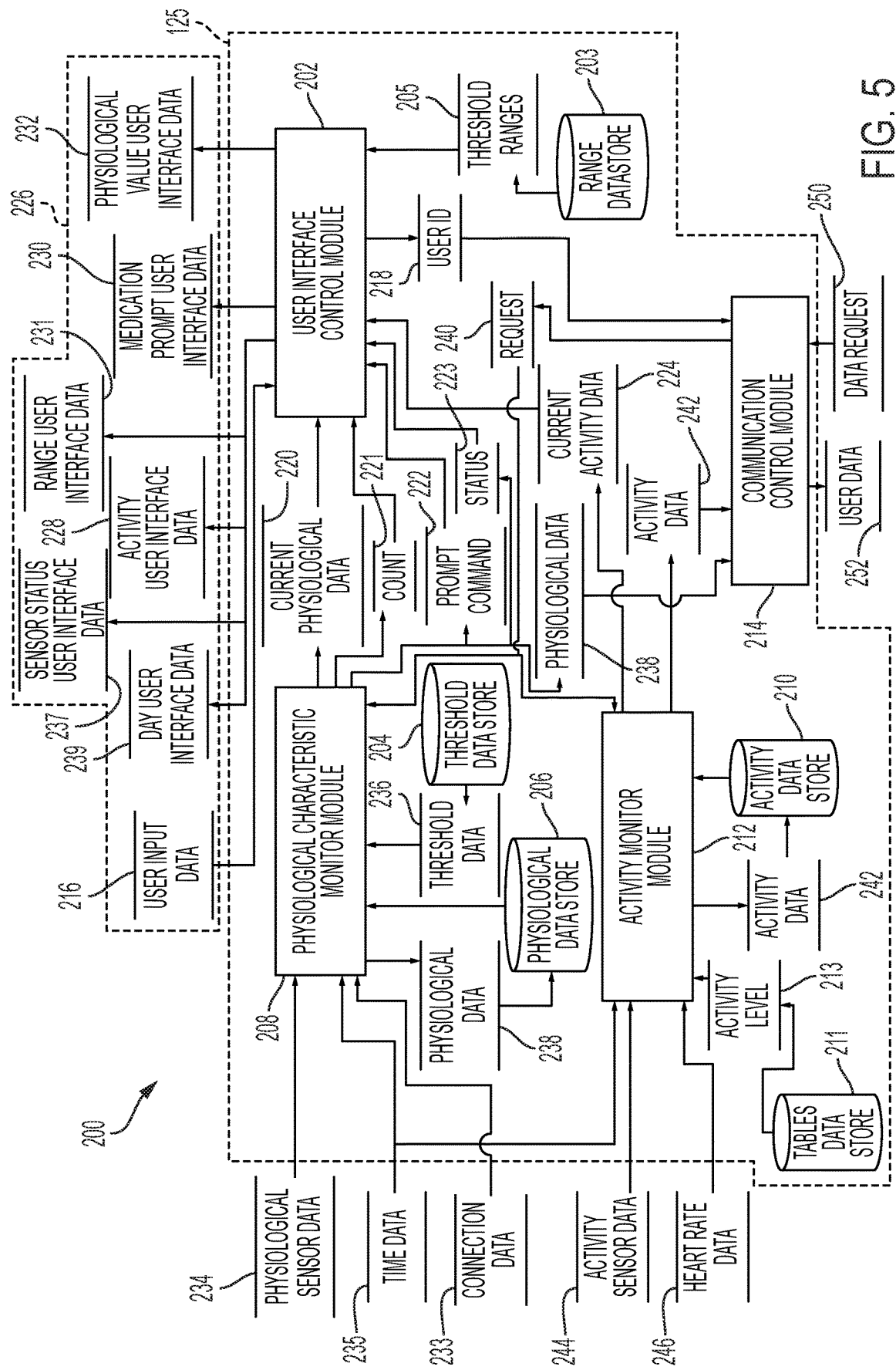
FIG. 5 is a dataflow diagram illustrating a wearable device monitoring system of the physiological characteristic monitoring system of FIG. 1, which may be implemented by a controller of the wearable device in accordance with various embodiments.

For example, as shown in more detail with regard to FIG. 5, and with continued reference to FIG. 4, a dataflow diagram illustrates various embodiments of a wearable device monitoring system 200 of the physiological characteristic monitoring system 100, which may be embedded within the controller 125 of the wearable device 102. Various embodiments of the wearable device monitoring system 200 according to the present disclosure can include any number of sub-modules embedded within the controller 125. As can be appreciated, the sub-modules shown in FIG. 5 may be combined and/or further partitioned to similarly receive data from the physiological characteristic sensor 104, the activity sensor 116 and the heart rate sensor 118, and output data and one or more user interfaces. Inputs to the wearable device monitoring system 200 may be received from the user interface 122 (FIG. 4), received from the physiological characteristic sensor 104 (FIG. 4), the activity sensor 116 (FIG. 4) and the heart rate sensor 118 (FIG. 4), received from other control modules (not shown) associated with the physiological characteristic monitoring system 100, and/or determined/modeled by other sub-modules (not shown) within the controller 125. In various embodiments, with reference to FIG. 5, the wearable device monitoring system 200 includes a user interface (UI) control module 202, a range datastore 203, a threshold datastore 204, a physiological datastore 206, a physiological characteristic monitor module 208, an activity datastore 210, a tables datastore 211, an activity monitor module 212 and a communication control module 214.

The range datastore 203 stores threshold range data for the physiological characteristic. In one example, the range datastore 203 stores threshold ranges 205 that provide a normal range for a blood glucose level, a caution range for a blood glucose level and a warning range for a blood glucose level. In one example, the normal range is about 70 milligrams per deciliter (mg/dL) to about 120 milligrams per deciliter (mg/dL). The caution range is a predetermined or predefined range outside of the normal range, as predefined by American Diabetic Association (ADA) guidelines and/or one or more physicians. The warning range is a predetermined or predefined range outside of the caution range, as predefined by American Diabetic Association (ADA) guidelines and/or one or more physicians.

The UI control module 202 receives user input data 216. The user input data 216 is input data received by the user's interaction with the user interface 122. The UI control module 202 processes the user input data 216 and sets user identification (ID) 218 for the communication control module 214. The user ID 218 is a unique identifier of the user of the wearable device 102, including, but not limited to, a name, a birthday, a pin number, etc. The UI control module 202 also processes the user input data 216 for a shutdown request. The shutdown request is a request to power down the wearable device 102. The UI control module 202 also processes the user input data 216 to receive a number of days that the physiological characteristic sensor 104 will be worn by the user. The UI control module 202 stores the number of days in a memory associated with the UI control module 202.

The UI control module 202 also receives as input current physiological data 220 and prompt command 222 from the physiological characteristic monitor module 208. The current physiological data 220 is a current physiological characteristic level as observed by the physiological characteristic sensor 104. The prompt command 222 is a command to output a prompt for medicine, for example, insulin, as will be discussed. Generally the prompt command 222 is generated and output by the physiological characteristic monitor module 208 based on physiological sensor data 234 received from the physiological characteristic sensor 104. The UI control module 202 also receives as input current activity data 224 from the activity monitor module 212. The current activity data 224 is a current activity level of the user determined by the activity monitor module 212 based on sensor signals received from the activity sensor 116 and/or sensor signals received from the heart rate sensor 118.

The UI control module 202 receives as input count 221 from the physiological characteristic monitor module 208. The count 221 is a current number of days that the physiological characteristic sensor 104 has been coupled to the body B of the user. The UI control module 202 also receives as input status 223 from the physiological characteristic monitor module 208. The status 223 indicates a condition of the physiological characteristic sensor 104, including, but not limited to, sensor working, sensor not working, replace sensor, etc.

Based on the current physiological data 220, the prompt command 222, the current activity data 224, the count 221 and/or the status 223, the UI control module 202 generates and outputs user interface data 226 for rendering a user interface on the display 130 (FIG. 4). In one example, the user interface data 226 includes an activity user interface data 228, a medication prompt user interface data 230, a physiological value user interface data 232, a range user interface data 231, a sensor status user interface data 237 and a day user interface data 239. The activity user interface data 228 includes instructions for rendering on the display 130 a graphical representation of the user's current activity level based on the current activity data 224. The medication prompt user interface data 230 includes instructions for rendering on the display 130 a textual prompt for the user to take medicine based on the receipt of the prompt command 222. The physiological value user interface data 232 includes instructions for rendering on the display 130 a graphical representation of the user's current physiological value based on the current physiological data 220.

In one example, in order to generate the range user interface data 231, the UI control module 202 retrieves threshold ranges 205 from the range datastore 203. The UI control module 202 compares the current physiological data 220 to the threshold ranges 205, and determines whether the current physiological data 220 is within the normal range. If true, the UI control module 202 generates and outputs the range user interface data 231 for rendering a range value user interface on the display that graphically and/or textually indicates the user's blood glucose is within the normal range. For example, the range value user interface includes a green symbol, such as an arrow, when the current physiological data 220 is within the normal range. The UI control module 202 also compares the current physiological data 220 to the threshold ranges 205, and determines whether the current physiological data 220 is within the caution range. If true, the UI control module 202 generates and outputs the range user interface data 231 for rendering a range value user interface on the display that graphically and/or textually indicates the user's blood glucose is within the caution range. For example, the range value user interface includes a yellow symbol, such as an arrow, when the current physiological data 220 is within the caution range. The UI control module 202 also compares the current physiological data 220 to the threshold ranges 205, and determines whether the current physiological data 220 is within the warning range. If true, the UI control module 202 generates and outputs the range user interface data 231 for rendering a range value user interface on the display that graphically and/or textually indicates the user's blood glucose is within the warning range. For example, the range value user interface includes a red symbol, such as an arrow, when the current physiological data 220 is within the warning range.

The UI control module 202 also generates and outputs the sensor status user interface data 237 for rendering a status user interface on the display 130 based on the status 223. In one example, the sensor status user interface data 237 includes a graphical representation and/or textual message of the condition of the physiological characteristic sensor 104. For example, the sensor status user interface data 237 provides instructions for rendering the status user interface with "Replace Sensor" on the display 130. In other example, the sensor status user interface data 237 provides instructions for rendering the status user interface with "Check Sensor" on the display 130. As a further example, the sensor status user interface data 237 provides instructions for rendering the status user interface with a symbol that indicates the current condition of the physiological characteristic sensor 104 is good or working.

The UI control module 202 also generates and outputs the day user interface data 239 for rendering a day user interface on the display 130. In one example, based on the count 221, the UI control module 202 subtracts the value of the count 221 from the number of days received from the user input data 216 to determine a number of days remaining for which the physiological characteristic sensor 104 will be coupled to the body B of the user. The UI control module 202 generates and outputs the day user interface data 239 based on the number of days remaining for which the physiological characteristic sensor 104 will be coupled to the body B of the user. Thus, in this example, the day user interface data 239 includes instructions for rendering a value of the number of remaining days on the display 130.

The threshold datastore 204 stores threshold value data for the physiological characteristic. In one example, the threshold datastore 204 stores threshold data 236 that includes a threshold minimum value and a threshold maximum value for a blood glucose level. The threshold data 236 (the threshold minimum value and the threshold maximum value) stored in the threshold datastore 204 are predefined, and factory set values. In one example, the threshold minimum value is about 70 milligrams per deciliter (mg/dL); and the threshold maximum value is about 180 milligrams per deciliter (mg/dL).

The physiological datastore 206 stores physiological data 238 associated with the value of the physiological characteristic as observed by the physiological characteristic sensor 104. In one example, the physiological datastore 206 is populated by the physiological characteristic monitor module 208 based on the sensor signals or sensor data received by the physiological characteristic sensor 104.

The physiological characteristic monitor module 208 receives as input connection data 233. The connection data 233 comprises a signal or data that indicates that the sensor connector 138 of the physiological characteristic sensor 104 is received within and connected to the connector 114 of the wearable device 102. Based on the receipt of the connection data 233, the physiological characteristic monitor module 208 receives as input the physiological sensor data 234 and time data 235. The physiological sensor data 234 comprises the sensor signals or sensor data from the physiological characteristic sensor 104. The time data 235 is a current day and time, which may be received from other modules of the controller 125. The physiological characteristic monitor module 208 processes the physiological sensor data 234, and determines a current value of the physiological characteristic. Based on the current value of the physiological characteristic, the physiological characteristic monitor module 208 sets the current physiological data 220 for the UI control module 202. The physiological characteristic monitor module 208 also associates the current value of the physiological characteristic with the current day and time, and stores the associated data as the physiological data 238 in the physiological datastore 206.

Based on the current value of the physiological characteristic, the physiological characteristic monitor module 208 also retrieves the threshold data 236 from the threshold datastore 204. The physiological characteristic monitor module 208 compares the current value of the physiological characteristic to the threshold minimum value and the threshold maximum value. If the current value of the physiological characteristic is less than the threshold minimum value, the physiological characteristic monitor module 208 sets the prompt command 222 for the UI control module 202. If the current value of the physiological characteristic is greater than the threshold maximum value, the physiological characteristic monitor module 208 also sets the prompt command 222 for the UI control module 202.

The physiological characteristic monitor module 208 also receives as input a request 240 from the communication control module 214. The request 240 is a command to provide data. Based on the receipt of the request 240, the physiological characteristic monitor module 208 retrieves the physiological data 238 from the physiological datastore 206 and sets the retrieved physiological data 238 for the communication control module 214.

The activity datastore 210 stores activity data 242 associated with the activity level of the user as observed by the activity sensor 116 and/or the heart rate sensor 118. In one example, the activity datastore 210 is populated by the activity monitor module 212 based on the sensor signals or sensor data received by the activity sensor 116 and/or the heart rate sensor 118.

The tables datastore 211 stores one or more tables (e.g., lookup tables) that indicate a current level of activity of the user based on a heart rate and an acceleration of the wearable device 102. In other words, the tables datastore 211 stores one or more tables that provide one or more predefined activity levels 213 for the user based on the acceleration observed by the activity sensor 116 and/or the heart rate observed by the heart rate sensor 118. In various embodiments, the tables may be interpolation tables that are defined by one or more indexes. One or more activity levels 213 provided by at least one of the tables generally indicates whether the user is exercising, resting, sleeping, etc. As an example, one or more tables can be indexed by various parameters such as, but not limited to, heart rate or acceleration, to provide the one or more activity levels 213.

The activity monitor module 212 receives as input activity sensor data 244, heart rate data 246 and the time data 235. The activity sensor data 244 comprises the sensor signals or sensor data from the activity sensor 116. The heart rate data 246 comprises the sensor signals or sensor data from the heart rate sensor 118. The activity monitor module 212 processes the activity sensor data 244, for example, to determine a current acceleration of the wearable device 102; and processes the heart rate data 246, for example, to determine a current heart rate of the user. Based on the current acceleration of the wearable device 102 and the current heart rate of the user, the activity monitor module 212 queries the tables datastore 211 and retrieves the activity level 213 of the user. Thus, the activity monitor module 212 determines the current activity level 213 of the user based on the activity sensor data 244 and the heart rate data 246. The activity monitor module 212 sets the retrieved activity level 213 of the user as the current activity data 224 for the UI control module 202. The activity monitor module 212 also associates the current activity level 213 of the user with the current day and time, and stores the associated data as the activity data 242 in the activity datastore 210.

The activity monitor module 212 also receives as input the request 240 from the communication control module 214. Based on the receipt of the request 240, the activity monitor module 212 retrieves the activity data 242 from the activity datastore 210 and sets the retrieved activity data 242 for the communication control module 214.

The communication control module 214 receives as input a data request 250. The data request 250 is a request for data regarding the value of the physiological characteristic and activity level of the user, which is received from the communication system 124. In one example, the data request 250 is output from the portable device communication system 152 of the portable electronic device 106 and received by the communication system 124 of the wearable device 102. Based on the data request 250, the communication control module 214 sets the request 240 for the physiological characteristic monitor module 208 and the activity monitor module 212.

The communication control module 214 receives as input the physiological data 238 and the activity data 242. The communication control module 214 also receives as input the user ID 218 from the UI control module 202. The communication control module 214 associates the user ID 218 with the physiological data 238 and the activity data 242, and outputs this associated data as user data 252 for communication to the portable electronic device 106. Thus, the user data 252 comprises the physiological data 238 and the activity data 242 for the identified user.

Figure 6:
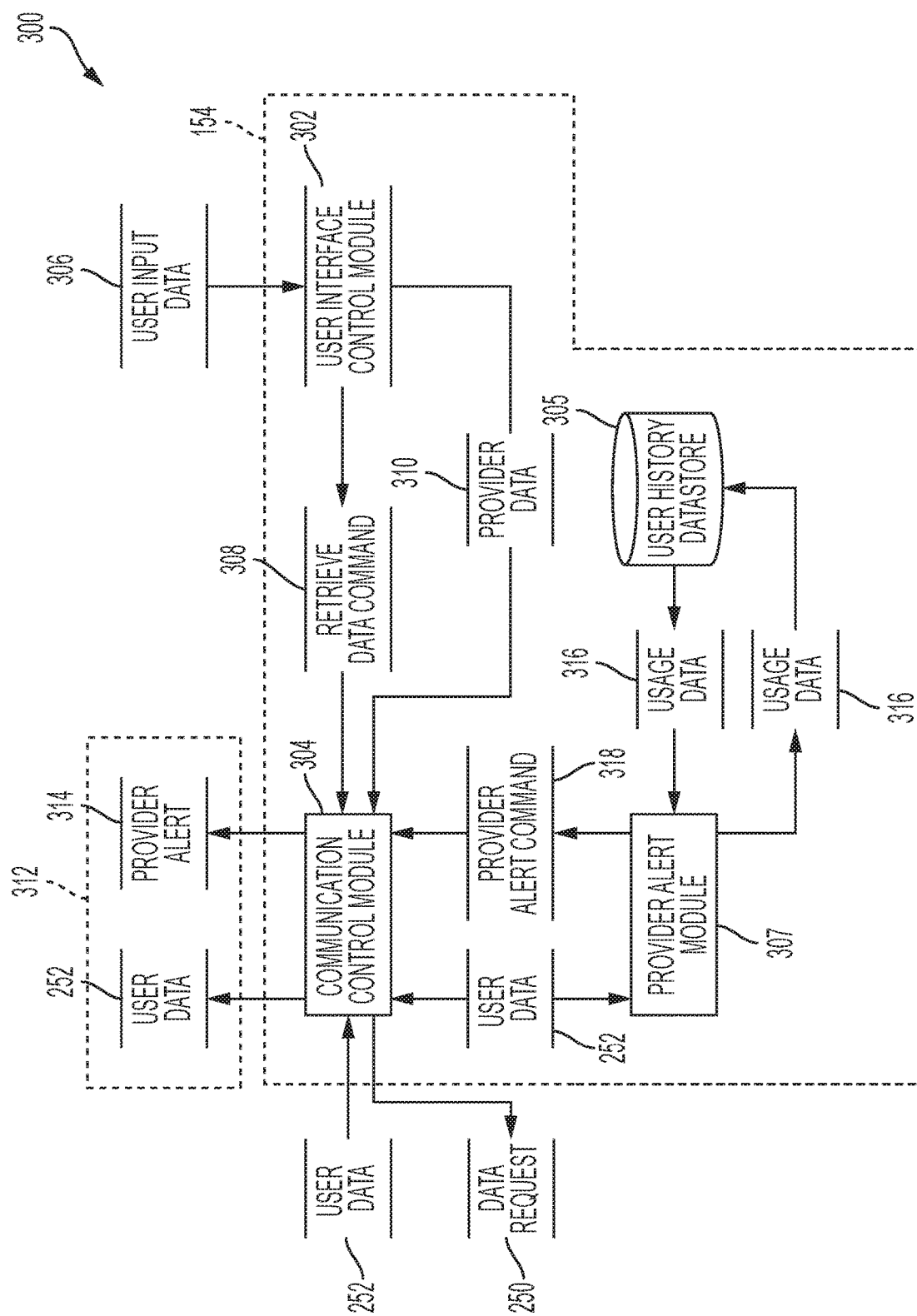
FIG. 6 is a dataflow diagram illustrating a portable device monitoring system of the physiological characteristic monitoring system of FIG. 1, which may be implemented by a controller of the portable electronic device in accordance with various embodiments.

As shown in more detail with regard to FIG. 6, and with continued reference to FIGS. 4 and 5, a dataflow diagram illustrates various embodiments of a portable device monitoring system 300 of the physiological characteristic monitoring system 100, which may be embedded within the portable device controller 154 of the portable electronic device 106. Various embodiments of the portable device monitoring system 300 according to the present disclosure can include any number of sub-modules embedded within the portable device controller 154. As can be appreciated, the sub-modules shown in FIG. 6 may be combined and/or further partitioned to similarly receive data from the wearable device 102 (FIG. 4), and output data to a medical provider. Inputs to the portable device monitoring system 300 may be received from the portable device user interface 150 (FIG. 4), received from the wearable device 102 (FIG. 4), received from other control modules (not shown) associated with the physiological characteristic monitoring system 100, and/or determined/modeled by other sub-modules (not shown) within the portable device monitoring system 300. In various embodiments, with reference to FIG. 6, the portable device monitoring system 300 includes a user interface (UI) control module 302, a communication control module 304, a user history datastore 305 and a provider alert module 307.

The UI control module 302 receives user input data 306. The user input data 306 is input data received by the user's interaction with the portable device user interface 150. The UI control module 302 processes the user input data 306 and sets a retrieve data command 308 for the communication control module 304. The retrieve data command 308 is a command to retrieve data from the wearable device 102. The UI control module 302 also processes the user input data 306 and sets provider data 310 for the communication control module 304. The provider data 310 includes an identifier and contact information for a medical provider. For example, the provider data 310 includes, but is not limited to, a name, email address, etc. associated with a medical provider of the user.

The communication control module 304 receives as input the retrieve data command 308. Based on the retrieve data command 308, the communication control module 304 outputs the data request 250. The communication control module 304 receives as input the provider data 310 and the user data 252. Based on the receipt of the user data 252, the communication control module 304 outputs medical data 312 to the medical provider identified in the provider data 310. The medical data 312 includes the user data 252, which comprises the values of the physiological characteristic and the values of the activity levels of the user for particular days and times. In certain instances, the medical data 312 also includes a provider alert 314. The provider alert 314 may indicate that a user may need medical intervention. In this regard, the communication control module 304 receives as input a provider alert command 318 from the provider alert module 307. Based on the provider alert command 318, the communication control module 304 outputs the provider alert 314 in the medical data 312 for the provider.

The user history datastore 305 stores usage data 316, which is the user data 252 received from the wearable device 102 and associated with a period of use of the wearable device 102 and physiological characteristic sensor 104 on the body B of the user. In one example, the user history datastore 305 is populated by the provider alert module 307 based on the user data 252 received from the communication control module 304.

The provider alert module 307 receives as input the user data 252. Based on the user data 252, the provider alert module 307 determines the period of use of the wearable device 102 and physiological characteristic sensor 104 on the body B of the user, for example, by determining a start time and date, and an end time and date based on the physiological data 238. The provider alert module 307 associates the determined period of use with the user data 252, and stores this as the usage data 316 in the user history datastore 305.

Based on the user data 252, the provider alert module 307 also retrieves a prior usage data 316 from the user history datastore 305. In one example, the provider alert module 307 retrieves the usage data 316 for the period of use of the wearable device 102 and physiological characteristic sensor 104 immediately prior to the current use of the wearable device 102 and physiological characteristic sensor 104 on the body B of the user. The provider alert module 307 compares the usage data 316 to the user data 252, and determines whether the user data 252 correlates with the usage data 316. Stated another way, the provider alert module 307 compares the usage data 316 from the prior use of the wearable device 102 and physiological characteristic sensor 104 to the user data 252 and determines whether there has been a change in physiological data 238 in the user data 252. In one example, the provider alert module 307 determines whether the difference between the usage data 316 and the user data 252 is greater than a threshold difference. The threshold difference is predefined or predetermined value, which may be stored in the user history datastore 305 or stored in a memory associated with the provider alert module 307. If the difference between the usage data 316 and the user data 252 is greater than the threshold difference, the provider alert module 307 sets the provider alert command 318 for the communication control module 304. The provider alert command 318 is a command to output the provider alert 314 based on a change in the physiological data 238 between the prior use of the wearable device 102 and physiological characteristic sensor 104 and the current use. It should be noted that while the provider alert module 307 is described herein as comparing the user data 252 to the usage data 316 for the period of use immediately prior to the current use, the provider alert module 307 may compare the user data 252 to any prior usage data 316 associated with the user.

It should be noted that while the provider alert module 307 is illustrated and described herein as being associated with the portable device controller 154 of the portable electronic device 106, in other embodiments, the provider alert module 307 may be associated with the controller 125 of the wearable device 102. In that embodiment, the wearable device 102 may generate the provider alert 314, which may be communicated, via the communication control module 214 of the wearable device 102 to the communication control module 304 of the portable electronic device 106.

Figure 7:
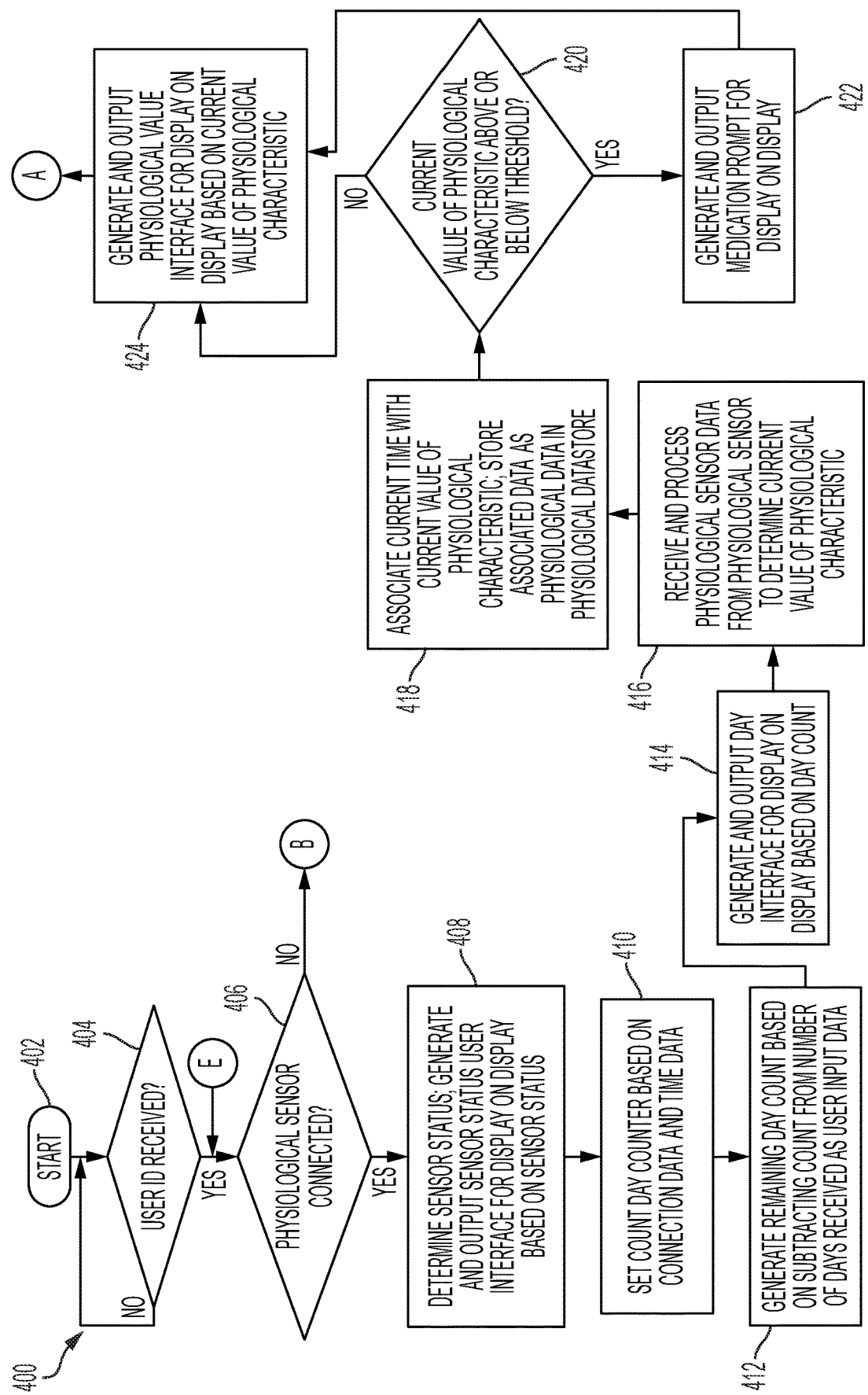
FIG. 7 is a flowchart illustrating a control method for the physiological characteristic monitoring system of FIG. 1, in accordance with various embodiments.
Figure 8:
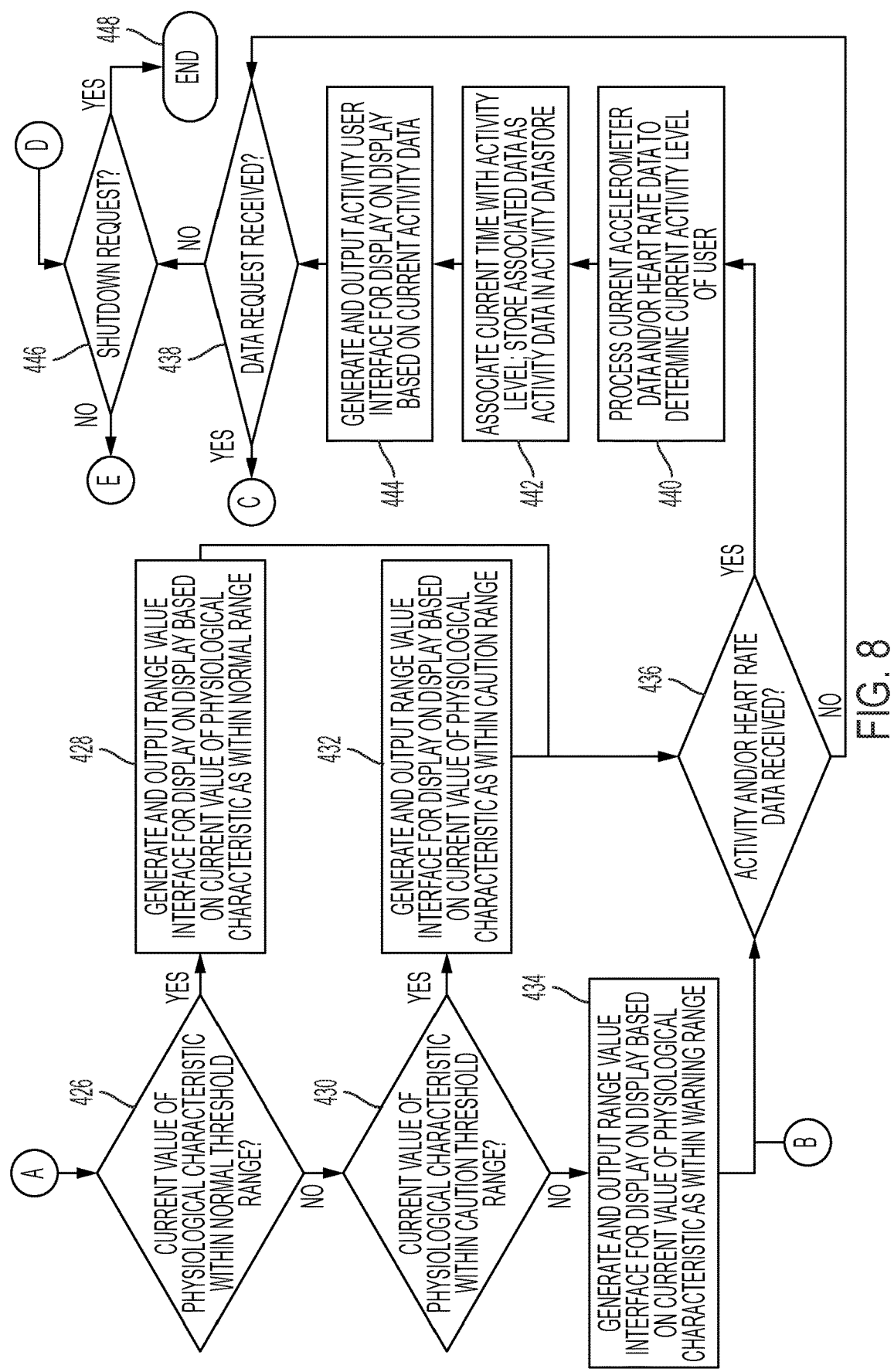
FIG. 8 is a continuation of the flowchart of FIG. 7, in accordance with various embodiments.
Figure 9:
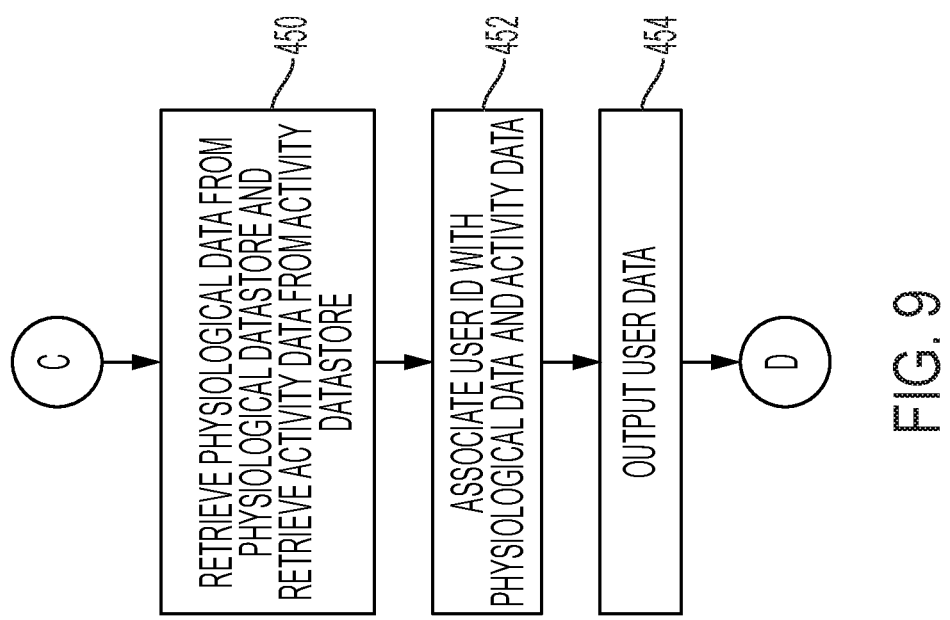
FIG. 9 is a continuation of the flowchart of FIG. 7, in accordance with various embodiments.

Referring now to FIGS. 7, 8 and 9, and with continued reference to FIGS. 1-5, a flowchart illustrates a control method 400 that can be performed by the wearable device monitoring system 200 of FIG. 5 of the physiological characteristic monitoring system 100 in accordance with the present disclosure. In various embodiments, the control method 400 is performed by the processor 132 of the controller 125. As can be appreciated in light of the disclosure, the order of operation within the method is not limited to the sequential execution as illustrated in FIGS. 7, 8 and 9, but may be performed in one or more varying orders as applicable and in accordance with the present disclosure. In various embodiments, the control method 400 can be scheduled to run based on one or more predetermined events, such as based on the receipt of the connection data 233.

With reference to FIG. 7, the method begins at 402. At 404, the method determines whether user ID 218 has been received as input to the UI control module 202. If true, the method proceeds to 406. Otherwise, the method loops.

At 406, the method determines whether the physiological characteristic sensor 104 is connected to the wearable device 102. In one example, the method determines whether the connection data 233 has been received. If true, the method proceeds to 408. Otherwise, the method proceeds to B on FIG. 8.

At 408, the method determines the status 223 of the physiological characteristic sensor 104. Based on the status 223, the method generates and outputs the sensor status user interface data 237 for rendering the sensor status user interface on the display 130. At 410, the method sets the count 221 for a value of the day based on the connection data 233 and time data 235. At 412, the method subtracts the value of the count 221 from the number of days for the user to wear the physiological characteristic sensor 104, which is received from the user input data 216. At 414, the method generates and outputs the day user interface data 239 for rendering the day user interface on the display 130. At 416, the method receives and processes the physiological sensor data 234 received from the physiological characteristic sensor 104. Based on the physiological sensor data 234, the method determines the current value of the physiological characteristic. At 418, the method receives the time data 235 and associates the current value of the physiological characteristic with the current day and time. The method stores the associated data as physiological data 238 in the physiological datastore 206.

At 420, the method retrieves the threshold data 236 from the threshold datastore 204 and determines whether the current value of the physiological characteristic is above or below the threshold for the value of the physiological characteristic. For example, the method determines whether the current value of the physiological characteristic is greater than the threshold maximum value. The method also determines if the current value of the physiological characteristic is less than the threshold minimum value. If the current value of the physiological characteristic is greater than the threshold maximum value or less than the threshold minimum value, the method proceeds to 422. Otherwise, the method, at 424, generates and outputs the physiological value user interface data 232 for rendering the current value of the physiological characteristic on the display 130. At 422, the method generates and outputs the medication prompt user interface data 230 for rendering the prompt for medicine on the display 130. The method proceeds to A on FIG. 8.

With reference to FIG. 8, FIG. 8 is a continuation of the flowchart of FIG. 7. From A on FIG. 8, at 426, the method retrieves the threshold ranges 205 from the range datastore 203 and determines whether the current value of the physiological characteristic is within the normal threshold range. If true, the method proceeds to 428. Otherwise, at 430, the method determines whether the current value of the physiological characteristic is within the caution threshold range. If true, the method proceeds to 432. Otherwise, at 434, the method determines that the current value of the physiological characteristic is within the warning threshold range. The method generates and outputs the range user interface data 231 for rendering the range value user interface on the display 130 that indicates that the current value of the physiological characteristic is within the warning range. At 428, the method generates and outputs the range user interface data 231 for rendering the range value user interface on the display 130 that indicates that the current value of the physiological characteristic is within the normal range. At 432, the method generates and outputs the range user interface data 231 for rendering the range value user interface on the display 130 that indicates that the current value of the physiological characteristic is within the caution range.

At 436, the method determines whether current activity data from the activity sensor 116 and/or current heart rate from the heart rate sensor 118 has been received. If false, the method proceeds to 438. Otherwise, if true, at 440, the method processes the sensor signals (i.e. activity sensor data 244) from the activity sensor 116 and/or the sensor signals (i.e. the heart rate data 246) from the heart rate sensor 118 and determines the current activity level of the user. In one example, based on the heart rate data 246 and the activity sensor data 244, the method queries the tables datastore 211 and retrieves the activity level 213. At 442, the method receives the time data 235 and associates the activity level 213 of the user with the current day and time. The method stores the associated data as activity data 242 in the activity datastore 210. At 444, the method generates and outputs the activity user interface data 228 for rendering the current activity level of the user on the display 130.

At 438, the method determines if a request for data (i.e. the data request 250) has been received from the portable electronic device 106. If true, the method proceeds to C on FIG. 9. Otherwise, at 446, the method determines whether a request to shutdown the wearable device 102 has been received, as user input data 216 via the user interface 122, for example. If true, the method ends at 448. Otherwise, the method proceeds to E on FIG. 7.

With reference to FIG. 9, FIG. 9 is a continuation of the flowchart of FIG. 8. From C on FIG. 9, at 450, the method retrieves the physiological data 238 from the physiological datastore 206 and retrieves the activity data 242 from the activity datastore 210. At 452, the method associates the user ID 218 with the physiological data 238 and the activity data 242. At 454, the method outputs the user data 252 for the portable electronic device 106. The method proceeds to D on FIG. 8.

Figure 10:
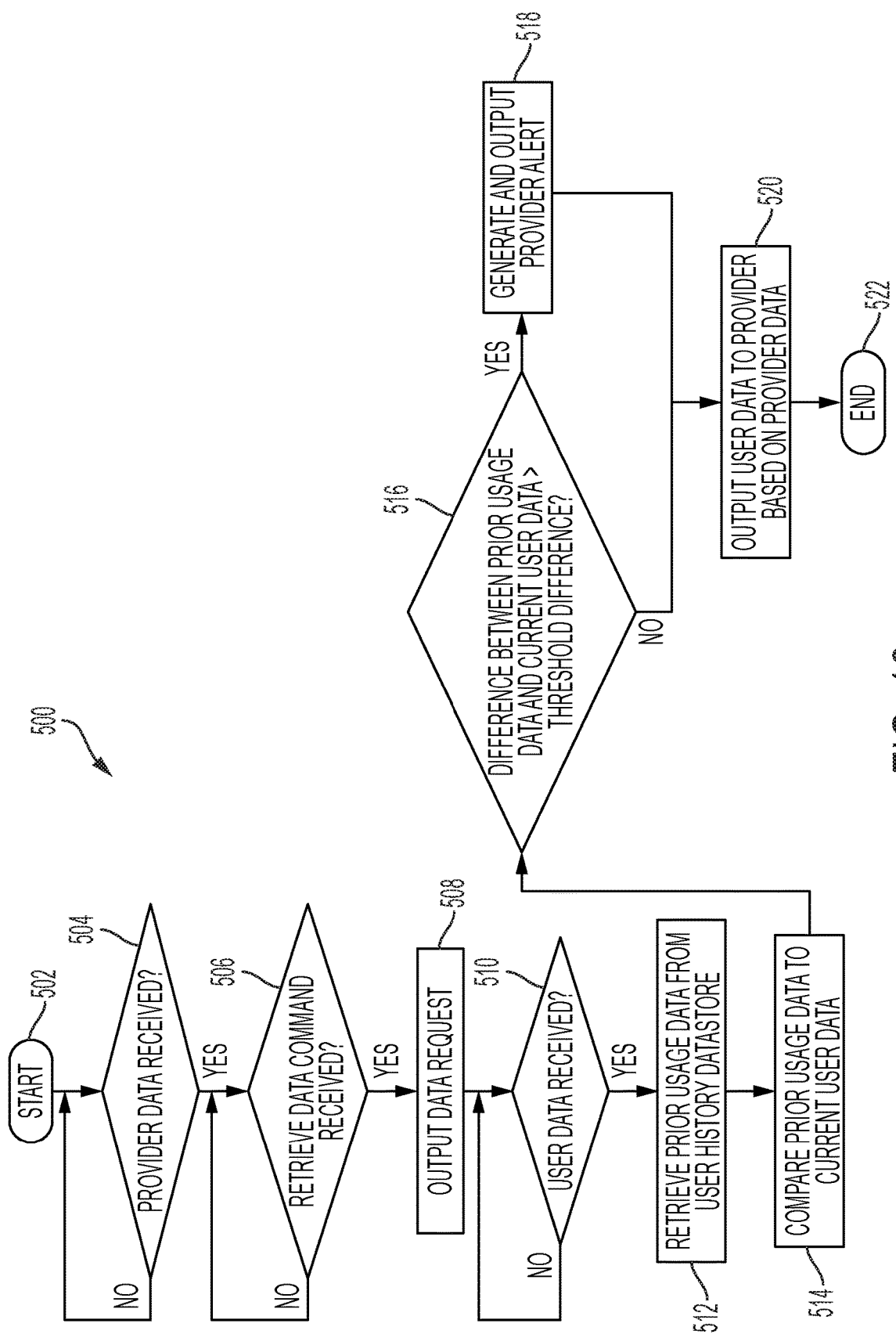
FIG. 10 is a flowchart illustrating a control method for the physiological characteristic monitoring system of FIG. 1, in accordance with various embodiments.

Referring now to FIG. 10, and with continued reference to FIGS. 1-4 and 6, a flowchart illustrates a control method 500 that can be performed by the portable device monitoring system 300 of FIG. 6 of the physiological characteristic monitoring system 100 in accordance with the present disclosure. In various embodiments, the control method 500 is performed by the processor 160 of the portable device controller 154. As can be appreciated in light of the disclosure, the order of operation within the method is not limited to the sequential execution as illustrated in FIG. 9, but may be performed in one or more varying orders as applicable and in accordance with the present disclosure. In various embodiments, the control method 500 can be scheduled to run based on one or more predetermined events, such as based on the receipt of the user input data 306.

The method begins at 502. At 504, the method determines whether provider data 310 has been received as input to the UI control module 302. If true, the method proceeds to 506. Otherwise, the method loops.

At 506, the method determines whether the retrieve data command 308 has been received as input to the UI control module 302. If true, the method proceeds to 508. Otherwise, the method loops.

At 508, the method outputs the data request 250 to the wearable device 102. At 510, the method determines whether the user data 252 has been received from the wearable device 102. If false, the method loops. If true, the method proceeds to 512. At 512, the method retrieves the usage data 316 from the user history datastore 305 for the period of use of the wearable device 102 and the physiological characteristic sensor 104 for the period immediately prior to the current use. At 514, the method compares the usage data 316 for the immediately prior use to the user data 252 for the current use of the wearable device 102 and the physiological characteristic sensor 104. At 516, the method determines whether the difference between the usage data 316 and the user data 252 is greater than a threshold difference. If true, the method generates and outputs the provider alert 314 at 518. Otherwise, at 520, the method outputs the user data 252 to the medical provider based on the provider data 310. The method ends at 522.

With reference to FIGS. 1-3, generally, the physiological characteristic sensor 104 is a disposable component, which is used a single time. The wearable device 102, however, is a reusable component, which the user can enjoy when the physiological characteristic sensor 104 is uncoupled from the wearable device 102. The reusable nature of the wearable device 102 enables the wearable device 102 to be uncoupled from a particular physiological characteristic sensor 104, and subsequently coupled to another physiological characteristic sensor 104, which enables the user to intermittently monitor their physiological characteristic, such as a BG level, as required by a medical provider. In one example, with the wearable device 102 formed and the attachment device 108 coupled to the wearable device 102, in order to couple the physiological characteristic sensor 104 to the wearable device 102, the attachment device 108 may be uncoupled from the coupling features 112. The physiological characteristic sensor 104 may be coupled to the wearable device 102 such that the sensor connector 138 is received within and coupled to the connector 114 of the wearable device 102. A backing layer, if provided over the adhesive patch 144 may be removed, and the physiological characteristic sensor 104 with the wearable device 102 coupled thereto may be positioned onto the body B of the user. An insertion device is coupled to the physiological characteristic sensor 104 and actuated to deploy the glucose sensor 140 into the body B of the user. With the physiological characteristic sensor 104 coupled to the wearable device 102, the physiological characteristic sensor 104 transfers data to and receives power from the wearable device 102.

Once the user has employed the physiological characteristic sensor 104 for a particular period of time, the physiological characteristic sensor 104 and the wearable device 102 may be removed from the body B of the user. The user may uncouple the sensor connector 138 from the connector 114 of the wearable device 102 by pulling the sensor connector 138 out of the connector 114. The user may re-attach the attachment device 108 by coupling the attachment device 108 to the coupling features 112, which enables the user to enjoy the wearable device 102 without the physiological characteristic sensor 104. The physiological characteristic sensor 104 may be properly disposed of. The user may also request data from the wearable device 102 to be sent to the portable electronic device 106.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A physiological characteristic monitoring system, comprising:
   a glucose sensing device comprising a glucose sensor, a sensor base having a first connector, and an adhesive patch coupled to the sensor base, the adhesive patch configured to adhere to skin of a user and to secure the glucose sensor to an anatomy of the user to sense glucose levels;
   a wearable band configured to be worn by the user, the wearable band being separate from the glucose sensing device and comprising a second connector; and
   a display device comprising a controller, a display, a third connector, and a fourth connector, wherein the third connector is complementary to the first connector and is configured to couple to and uncouple from the first connector such that the display device can attach to and detach from the glucose sensing device, and wherein the fourth connector is complementary to the second connector and is configured to couple to and uncouple from the second connector such that the display device can attach to and detach from the wearable band,
   wherein when the display device is attached to the glucose sensing device and is not attached to the wearable band, the controller is configured to cause the display to present at least a first user interface based on the glucose levels sensed by the glucose sensor, and
   wherein when the display device is attached to the wearable band and is not attached to the glucose sensing device, the controller is configured to cause the display to present at least a second user interface, the second user interface being different from the first user interface.

2. The physiological characteristic monitoring system of claim 1, further comprising an electronic device, wherein the electronic device is in communication with the display device.

3. The physiological characteristic monitoring system of claim 2, wherein the controller of the display device is configured to store the glucose levels in a physiological datastore and, based on a data request from the electronic device, the controller of the display device is configured to output stored glucose levels as user data for the electronic device.

4. The physiological characteristic monitoring system of claim 3, wherein based on the user data, the electronic device is configured to output an alert to a medical provider.

5. The physiological characteristic monitoring system of claim 1, wherein the display device further comprises at least one activity sensor configured to observe an activity level of the user and to generate sensor signals based on the observation, wherein the controller is configured to cause the display to present the second user interface based on the activity level of the user.

6. The physiological characteristic monitoring system of claim 1, wherein the first user interface includes an indication of a current glucose value sensed by the glucose sensor.

7. The physiological characteristic monitoring system of claim 6, wherein the controller of the display device is configured to determine whether the current glucose value exceeds a threshold, and to cause the display to present a prompt for the user to take medicine based on determining that the current glucose value exceeds the threshold.

8. The physiological characteristic monitoring system of claim 1, wherein the glucose sensing device is a continuous blood glucose monitor.

9. The physiological characteristic monitoring system of claim 8,
   wherein the glucose sensor is positioned within a subcutaneous tissue of the user.

10. The physiological characteristic monitoring system of claim 5, wherein the at least one activity sensor includes at least one of: an accelerometer or a heart rate sensor,
   wherein when the display device is attached to the wearable band and is not attached to the glucose sensing device, the controller is configured to cause the display to present the second user interface based on at least one of: an output of the accelerometer or an output of the heart rate sensor.

* * * * *